US00PP30883P3

(12) United States Plant Patent
Suzuki

(10) Patent No.: US PP30,883 P3
(45) Date of Patent: Sep. 17, 2019

(54) ***LOROPETALUM* PLANT NAMED 'SUZUKI'**

(50) Latin Name: *Loropetalum chinense*
Varietal Denomination: SUZUKI

(71) Applicant: Yuji Suzuki, Kawaguchi (JP)

(72) Inventor: Yuji Suzuki, Kawaguchi (JP)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,484

(22) Filed: Nov. 20, 2017

(65) Prior Publication Data

US 2019/0159393 P1 May 23, 2019

(51) Int. Cl.
*A01H 5/02* (2018.01)
*A01H 6/00* (2018.01)

(52) U.S. Cl.
USPC ..... Plt./226
CPC ..... *A01H 6/00* (2018.05); *A01H 5/02* (2013.01)

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Loropetalum* plant named 'SUZUKI' is disclosed, characterized by white flowers with a very sight pink flush, and strong heat tolerance and resistance to color change in extreme temperatures. Plant habit is very dense and full growing with very vibrant burgundy foliage. The new variety is a *Loropetalum*, normally produced as an outdoor garden or container plant.

3 Drawing Sheets

Latin name of the genus and species: *Loropetalum chinense.*

Variety denomination: 'SUZUKI'.

BACKGROUND OF THE INVENTION

The new *Loropetalum* cultivar is a product of a planned breeding program conducted by the inventor, Yuji Suzuki, in Kawaguchi City, Saitama, Japan. The objective of the breeding program was to produce new *Loropetalum* varieties with new colors and forms. The open pollination resulting in this new variety was made during 2005.

The seed parent is an unnamed, unpatented, *Loropetalum chinense*. The pollen parent is unidentified. The new variety was selected in 2013 by the inventor in a group of seedlings resulting from the 2005 open pollination, in a nursery in Kawaguchi City, Saitama, Japan.

Asexual reproduction of the new cultivar was performed by softwood terminal cuttings. This was first performed at a nursery in Kawaguchi City, Saitama, Japan, in June 2013 and has shown that the unique features of this cultivar are stable and reproduced true to type in 4 successive generations.

SUMMARY OF THE INVENTION

The cultivar 'SUZUKI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUZUKI'. These characteristics in combination distinguish 'SUZUKI' as a new and distinct *Loropetalum* cultivar:

1. Spring foliage color variegation.
2. White flowers with a very slight pink flush.
3. Compact and cascading plant habit.

PARENT COMPARISON

Plants of the new cultivar 'SUZUKI' are comparable to the seed parent in most horticultural characteristics. However, the new variety 'SUZUKI' differs in the following:

1. The new variety produces variegated foliage of pink, green and white, the seed parent has solid colored foliage.

COMMERCIAL COMPARISON

Plants of the new cultivar 'SUZUKI' are comparable to the patented, commercial variety *Loropetalum* 'Shang-hi' U.S. Plant Pat. No. 18,331. The two *Loropetalum* varieties are similar in most horticultural characteristics; however, the new variety 'SUZUKI' differs in the following:

1. The new variety produces variegated foliage of pink, green and white, this comparator produces solid dark purple foliage.
2. The new variety produces white flowers, very lightly flushed pink. This comparator produces pink flowers.

BRIEF DESCRIPTION OF THE PHOTOGRAPHS

The accompanying photograph in FIG. 1 illustrates in full color an overhead view of a typical plant of 'SUZUKI' grown in a 2 gallon pot.

Figure 1:
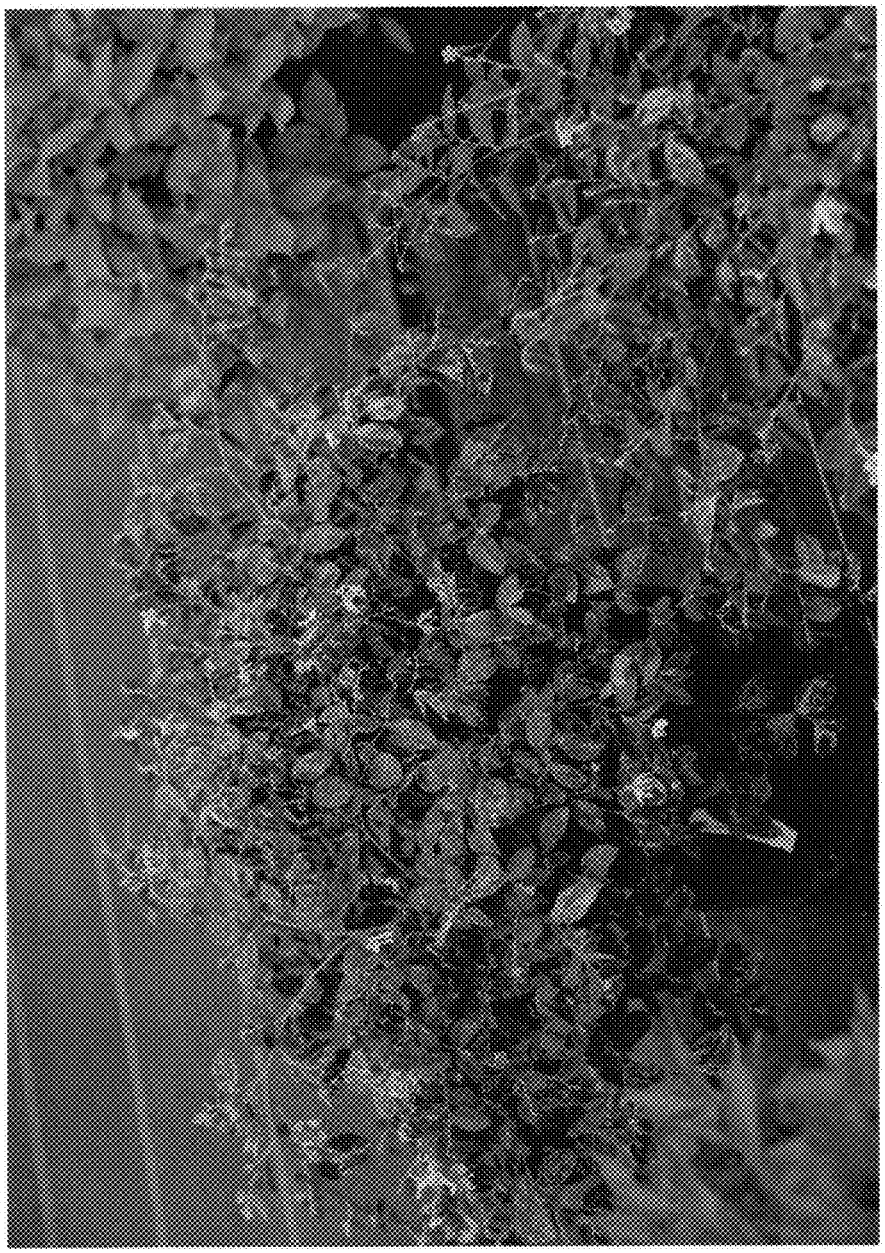
Figure 2:
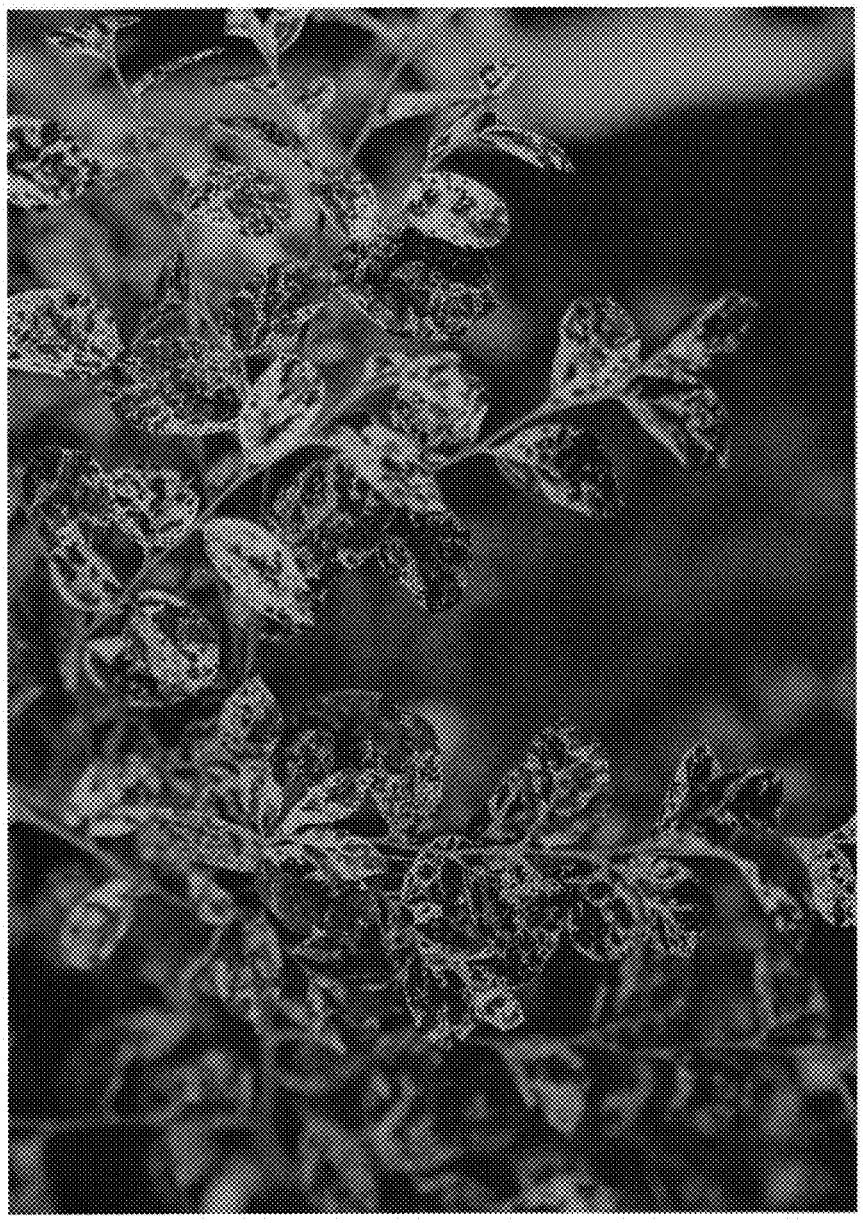
FIG. 2 illustrates a close-up view of the foliage.
Figure 3:
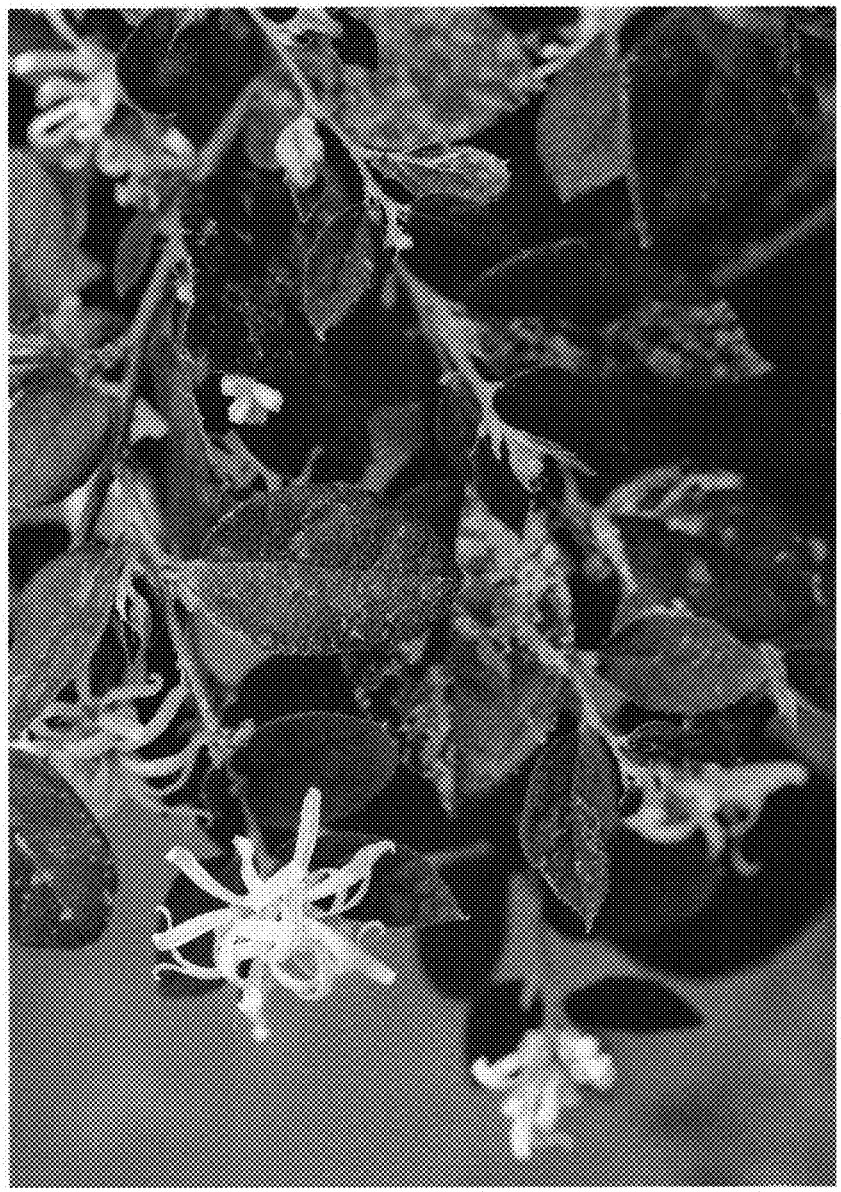
FIG. 3 illustrates a close-up view of the flowers and foliage. Age of the plant photographed is approximately 1 to 2 years old from a rooted cutting.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SUZUKI' plants grown in a poly greenhouse, in Grand Haven, Mich. The growing temperature averaged from 18-27° C. during the day and from 5-10° C. during the night. The poly was present from Fall through Winter, then removed in the Spring. Shade cloth was used through the Summer. Measurements and numerical values represent averages of typical plant types.

Botanical classification: *Loropetalum chinense* 'SUZUKI'.

PROPAGATION

Type of propagation typically used: Vegetative terminal cutting.

Time to initiate roots: 18 Days at 27° C.

Number of days to produce a rooted liner in Summer: 110 days at 27° C.

Root description: Thin to thick, fibrous, free branching and fleshy. New roots are purple in color, aging to brown. Not accurately measured with the R.H.S. chart.

PLANT

Type of plant: Perennial shrub.

Age of plant described: 2 to 3 years old.

Container size of the plant described: 3 gallon.

Growth habit: Semi-upright, mounded, cascading lower branches.

Height: 23 cm.

Plant spread: 76 cm.

Growth rate: Good.

Plant vigor: Good.

Branching characteristics: Horizontal Branches originating from base.

Characteristics of primary lateral branches:

- *Length.*—37 cm.
- *Quantity.*—20.
- *Diameter.*—4.5 cm.
- *Stem color.*—Greyed-brown 199B.
- *Aspect.*—0-90, mostly horizontal branches.
- *Strength.*—Good.
- *Texture.*—Glabrous.

Internode length: 1.5-2 cm.

Stem pubescence: No.

FOLIAGE

Leaf:

- *Arrangement.*—Alternate, single.
- *Average length.*—3 cm.
- *Average width.*—2.75 cm.
- *Shape of blade.*—Elliptic.
- *Apex.*—Acute.
- *Base.*—Obtuse.
- *Margin.*—Entire to partially sinuate.
- *Texture of top surface.*—Slightly rough.
- *Texture of bottom surface.*—Slightly rough.
- *Color.*—Young foliage upper side: Spring Variegation: Red-Purple N74D with spots of Violet-Blue N92A and Greyed-Purple 184C. Summer/Fall: Greyed-Purple N187A. Young foliage under side: Spring variegation: Red purple 73C with spots of Purple group N77A. Summer/Fall: Greyed-Green 191A. Mature foliage upper side: Spring variegation: Some are Green 139A, some Brown 200A with spots of Red purple 65A and White group NN155A. Summer/Fall: Greyed-Purple N187A. Mature foliage under side: Spring variegation: Yellow Green 144A, some have spots of 186C. Summer/Fall: Greyed-Green 191A.
- *Venation.*—Type: Pinnate. Venation color upper side: Very depressed, color indistinguishable from foliage. Venation color under side: Yellow green 154B.
- *Petiole.*—Length: 3 mm. Diameter: 1 mm. Color: Greyed-green 195B.

FLOWER

Inflorescence and flower type and habit: Umbel.

Quantity of flowers per inflorescence: 3-4.

Flower type: Strap-shaped.

Flower aspect: Upwards and outwards.

Quantity of flowers per lateral stem: 15-20.

Quantity of flowers per plant: Around 100.

Natural flowering season: Spring-Summer.

Persistence: Self-Cleaning.

Fragrance: None.

Bud:

- *Shape.*—Orbicular.
- *Length.*—4 mm.
- *Diameter.*—4 mm.
- *Color.*—Greyed-Green 195B with some faint Greyed-Red 181D.

Petals:

- *Quantity per flower.*—4.
- *Shape.*—Linear.
- *Arrangement.*—Irregular whorl.
- *Margin.*—Entire.
- *Texture.*—Smooth, silky all surfaces.
- *Length.*—1.75 mm.
- *Width.*—3 mm.
- *Tip.*—Slightly retuse and petals are curled at the tips.
- *Color.*—When opening: Upper surface: Green-white 157C. Lower surface: Green-white 157C. Fully opened: Upper surface: White N155B lightly flushed Red 56C. Lower surface: White N155B lightly flushed Red 56C.

Sepals:

- *Quantity per flower.*—4.
- *Appearance.*—Slightly pubescent.
- *Texture.*—Slightly pubescent all surfaces.
- *Arrangement.*—Whorl.
- *Shape.*—Ovate and fused, slightly curled outward.
- *Length.*—4 mm.
- *Width.*—3 mm.
- *Tip.*—Entire (smooth).
- *Base.*—Acute, slightly reflexed.
- *Margin.*—Fused.
- *Color.*—Mature upper side: Greyed-Green 195B. Mature under side: Greyed-Green 195B.

Peduncle:

*Length*.—Average 2 to 5 cm.

*Diameter*.—3 mm.

*Texture*.—Slightly pubescent.

*Color*.—Near RHS Yellow-Green 145C.

*Orientation*.—Approximately 15 to 35 degrees angle of emergence, aspect straight.

*Strength*.—Strong and flexible.

REPRODUCTIVE ORGANS

Stamens:

*Number*.—4.

*Filament length*.—Average 1 mm.

*Filament color*.—Near RHS White 155C.

*Anthers*.—Shape: Linear. Length: Less than 1 mm. Color: Near RHS White 155C. Pollen: Amount: Scant. Color: Near RHS White 155B.

Pistil:

*Number*.—2.

*Length*.—Approximately 1 mm.

*Style*.—Length: Less than 1 mm. Color: Near RHS White 155C.

*Stigma*.—Shape: Linear. Color: Near RHS White 155C. Ovary: Less than 1 mm, colored near Yellow-Green 150D.

OTHER CHARACTERISTICS

Lowest temperature tolerance: 5 to 10° F.

Fruits and seeds: Not observed to date.

Disease/pest resistance: No unusual susceptibility or resistance to diseases or pests noted to date.

What is claimed is:

1. A new and distinct cultivar of *Loropetalum* plant named 'SUZUKI' as herein illustrated and described.

* * * * *